(12) United States Patent
Jacobsen et al.

(10) Patent No.: US 12,310,802 B2
(45) Date of Patent: May 27, 2025

(54) NANOFIBER ADHESIVES FOR NAVIGATION TRACKER FIXATION

(71) Applicant: Medtronic Navigation, Inc., Louisville, CO (US)

(72) Inventors: Bradley W. Jacobsen, Erie, CO (US); Andrew J. Wald, Denver, CO (US); Kristen H. Temnyk, Broomfield, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 793 days.

(21) Appl. No.: 17/369,448

(22) Filed: Jul. 7, 2021

(65) Prior Publication Data

US 2022/0039906 A1 Feb. 10, 2022

Related U.S. Application Data

(60) Provisional application No. 63/060,937, filed on Aug. 4, 2020.

(51) Int. Cl.
*A61B 90/00* (2016.01)
*A61B 34/20* (2016.01)
(Continued)

(52) U.S. Cl.
CPC .............. *A61B 90/39* (2016.02); *A61B 34/20* (2016.02); *D01D 5/0007* (2013.01);
(Continued)

(58) Field of Classification Search
CPC . A61B 90/39; A61B 34/20; A61B 2034/2051; A61B 2090/3966;
(Continued)

(56) References Cited

U.S. PATENT DOCUMENTS 4,144,890 A * 3/1979 Hess .................... A61N 1/0587
607/130
6,428,206 B1 8/2002 Watanabe
(Continued)

FOREIGN PATENT DOCUMENTS

CN 108671418 10/2018
DE 102015202082 12/2015
(Continued)

OTHER PUBLICATIONS

Canon Medical US, Alphenix Biplane—Multi-Access Biplane System, YouTube.com, viewed Jul. 13, 2021 ,Jan. 8, 2019.
(Continued)

*Primary Examiner* — Rochelle D Turchen
(74) *Attorney, Agent, or Firm* — Harness, Dickey & Pierce, P.L.C.

(57) ABSTRACT

A tracker system for use in image guided surgery is disclosed. The tracker system may couple to wet tissue and may include a navigation tracker and a base pad that couple to each other. The base pad may be fabricated from a plurality of nonwoven nanofibers. The base pad is configured to couple to body tissue of a patient via at least one of adsorption, hydration equilibrium, and macromolecular interpenetration.

21 Claims, 5 Drawing Sheets

(51) Int. Cl.
*D01D 5/00* (2006.01)
*B82Y 5/00* (2011.01)
*B82Y 15/00* (2011.01)
*B82Y 40/00* (2011.01)

(52) U.S. Cl.
CPC .............. *A61B 2034/2051* (2016.02); *A61B 2090/3966* (2016.02); *A61B 2090/3979* (2016.02); *A61B 2090/3983* (2016.02); *B82Y 5/00* (2013.01); *B82Y 15/00* (2013.01); *B82Y 40/00* (2013.01); *D10B 2331/041* (2013.01); *D10B 2401/20* (2013.01)

(58) Field of Classification Search
CPC .... A61B 2090/3979; A61B 2090/3983; B82Y 5/00; B82Y 15/00; B82Y 40/00; D10B 2401/20
See application file for complete search history.

(56) References Cited

U.S. PATENT DOCUMENTS

| | | | |
|---|---|---|---|
| 6,461,039 B1 | 10/2002 | Klotz et al. | |
| 7,170,972 B2 | 1/2007 | Altman | |
| 7,300,205 B2 | 11/2007 | Grady | |
| 7,338,207 B2 | 3/2008 | Gregerson et al. | |
| 7,354,196 B2 | 4/2008 | Boese et al. | |
| 7,434,996 B2 | 10/2008 | Wang et al. | |
| 7,803,574 B2 | 9/2010 | Desai et al. | |
| 8,303,181 B2 | 11/2012 | Sukovic et al. | |
| 8,428,675 B2 | 4/2013 | McKenna | |
| 8,480,729 B2 | 7/2013 | Atanasoska et al. | |
| 9,474,831 B2 | 10/2016 | Boyden et al. | |
| 9,554,761 B2 | 1/2017 | Baumann et al. | |
| 9,855,016 B2 | 1/2018 | Lee | |
| 10,264,995 B2 | 4/2019 | Brister et al. | |
| 10,390,777 B2 | 8/2019 | Risher-Kelly et al. | |
| 10,485,632 B1 | 11/2019 | Al-Ekrish et al. | |
| 10,517,553 B2 | 12/2019 | Barker et al. | |
| 10,573,023 B2 | 2/2020 | Crawford | |
| 2003/0072416 A1 | 4/2003 | Rasche et al. | |
| 2006/0171508 A1 | 8/2006 | Noda et al. | |
| 2007/0078480 A1 | 4/2007 | Belenkaya et al. | |
| 2011/0046461 A1 | 2/2011 | McKenna | |
| 2012/0186629 A1* | 7/2012 | Nowlan | H01L 31/048 438/66 |
| 2016/0338644 A1* | 11/2016 | Connor | A61B 5/1126 |
| 2016/0361015 A1 | 12/2016 | Wang et al. | |
| 2017/0086684 A1 | 3/2017 | Xue et al. | |
| 2017/0239393 A1 | 8/2017 | Yoon et al. | |
| 2018/0154213 A1* | 6/2018 | Chen | A61B 5/1122 |
| 2019/0000429 A1 | 1/2019 | Magana et al. | |
| 2019/0029629 A1 | 1/2019 | Johnson et al. | |
| 2019/0038365 A1 | 2/2019 | Soper et al. | |
| 2020/0146642 A1 | 5/2020 | Fortuna et al. | |

FOREIGN PATENT DOCUMENTS

| | | |
|---|---|---|
| DE | 102015207736 | 11/2016 |
| WO | 2006069322 | 6/2006 |
| WO | 2010135418 | 11/2010 |
| WO | 2015085011 | 6/2015 |
| WO | 2018033744 | 2/2018 |
| WO | 2018121629 | 7/2018 |

OTHER PUBLICATIONS

GE Healthcare, OEC Elite, Premium Digital Mobiel C-Arm Technical Data, GE OEC Medical Systems, Inc. Viewed Jul. 13, 2021 on YouTube , Nov. 2014.

Baskaran, et al., Doxycycline-Eluting Core-Shell Type Nanofiber-Covered Trachea Stent for Inhibition of Cellular Metalloproteinase and Its Related Fibrotic Stenosis, Pharmaceutics vol. 11, 8 421 ,Aug. 19, 2019.

Kim, et al., Bio-Inspired, Highly Stretchable and Conductive Dry Adhesives Based on 1D-2D Hybrid Carbon Nanocomposites for All-in-One ECG Electrodes, ACS Nano ,2016.

Liu, et al.,Bioinspired, Microstructured Silk Fibroin Adhesives for Flexible Skin Sensors, ACS Applied Materials & Interfaces, vol. 12(5) ,Jan. 13, 2020 ,5601-5609.

Ngoepe, et al., Integration of Biosensors and Drug Delivery Technologies for Early Detection and Chronic Management of Illness, Sensors (Basel, Switzerland) vol. 13, 6 ,Jun. 14, 2013 ,7680-713.

Wang, et al.,Toward Self-Powered Wearable Adhesive Skin Patch with Bendable Microneelel Array for Transdermal Drug Delivery, Advanced Science (Weinheim, Baden-Wurttemberg, Germany) vol. 3, 9 1500441 ,Apr. 19, 2016.

International Search Report and Written Opinion dated Jan. 24, 2022 for PCT/US2021/044228.

Masek, et al., Multi-Layered Nanofibrous Mucoadhesive Films for Buccal and Sublingual Administration of Drug-Delivery and Vaccination Nanoparticles—Important Step Towards Effective Mucosal Vaccines, Journal of Controlled Release, Elsivier Amsterdam NL, vol. 249 ,Jul. 25, 2016 ,183-195.

* cited by examiner

US 12,310,802 B2

NANOFIBER ADHESIVES FOR NAVIGATION TRACKER FIXATION

RELATED APPLICATION

The present application claims benefit of U.S. Provisional Patent Application No. 63/060,937, filed on Aug. 4, 2020 and titled, "NANOFIBER ADHESIVES FOR NAVIGATION TRACKER FIXATION," the contents of this application are hereby incorporated by reference in its entirety.

TECHNICAL FIELD

The present disclosure relates generally to the field of medical devices. More particularly, some embodiments relate to nanofiber adhesives to adhere medical devices to tissue.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
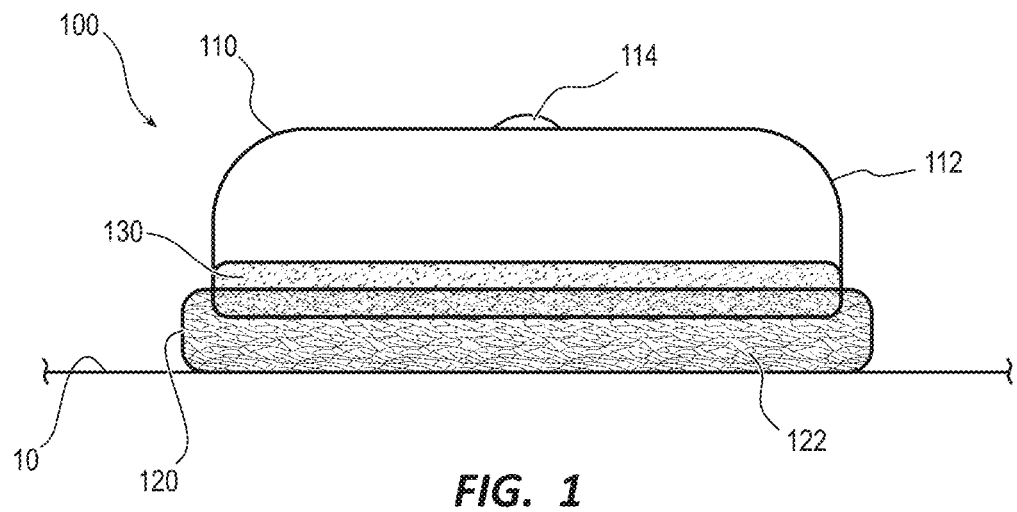
FIG. 1 is a side view of a tracker system attached to the tissue of a patient according to one embodiment of the present disclosure.

Medical practitioners may use surgical navigation systems during image guided navigation medical procedures. Patient trackers may be used in connection with these navigation systems to locate or identify anatomical structures and/or map those locations within a reference space. The ability to locate patient anatomical structures and/or map anatomical locations is established via patient registration. Registration refers to the computerized process used to match the three-dimensional position of the patient to the pre-operative and intra-operative images that are used for navigation. Such navigation systems may be used in a variety of procedures, including open procedures, minimally invasive procedures, and percutaneous procedures. Locations identified by patient trackers can then be used to guide treatment equipment to particular positions and orientations during a surgical operation and/or may be used to track the position or alignment of anatomical locations.

Some embodiments affix trackers to a patient. The location of these trackers are mapped within an image space (or reference space) for the patient, for example, by imaging those trackers along with a point of interest for therapy, such as a tumor. The trackers may then provide information to assist a surgeon in guiding and orienting therapeutic equipment with respect to the tumor. For example, some embodiments use electromagnetic trackers. During treatment, an electromagnetic field may be induced around the target location. The interaction between the patient trackers and the electromagnetic field may be used to determine the position and orientation (collectively, pose) of the tracker (e.g., with six degrees of freedom) within a reference space. The therapeutic equipment may also be controlled with respect to the same reference space. Thus, the patient trackers may be configured to provide one or more reference points for use during a procedure. In other embodiments, the trackers may use other approaches to provide pose information, such as infrared, radio, or ultrasound emitters/retroreflectors. Additional information regarding trackers may be found in at least at U.S. patent application Ser. No. 14/673,994, titled "Modular Coil Assembly," filed Mar. 31, 2015, which is hereby incorporated by reference in its entirety.

In some instances, patient trackers may be adhered to a patient's skin by adhesives or attached to bone by screws. While adhering a tracker to the skin is less invasive than bone screws, skin can shift significantly with respect to bone or other parts of the body between the time a tracker is placed and an initial image taken, and the time of a procedure. The skin can also shift with respect to bone or other parts of the body during the procedure. On the other hand, while screwing a tracker to bone generally provides a more positive, fixed position, that approach is relatively more invasive. A tracker that is fixable relative to bone or other parts of the body and is minimally invasive would be advantageous.

As further detailed below, trackers configured couple to thin tissues that are fixed to bone, such as (but not limited to) mucosal tissue or the periosteum of a bone, may be less invasive than screws while providing a more fixed location than adhesives on the skin. As such tissue may tend to be naturally wet, adhesion systems as detailed below may utilize wetting or hydration of an adherent to couple a patient tracker to the tissue.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, fluidic, electric/magnetic, and thermal interaction. Thus, two components may be coupled to each other even though they are not in direct contact with each other. The phrases "attached to" or "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms and are applied to medical devices as ordinarily used in that field. For example, the distal end of a medical device configured for direct manipulation by a practitioner is the end of the component that is furthest from the practitioner during ordinary use. The proximal end refers to the opposite end, or the end nearest the practitioner during ordinary use.

Figure 2:
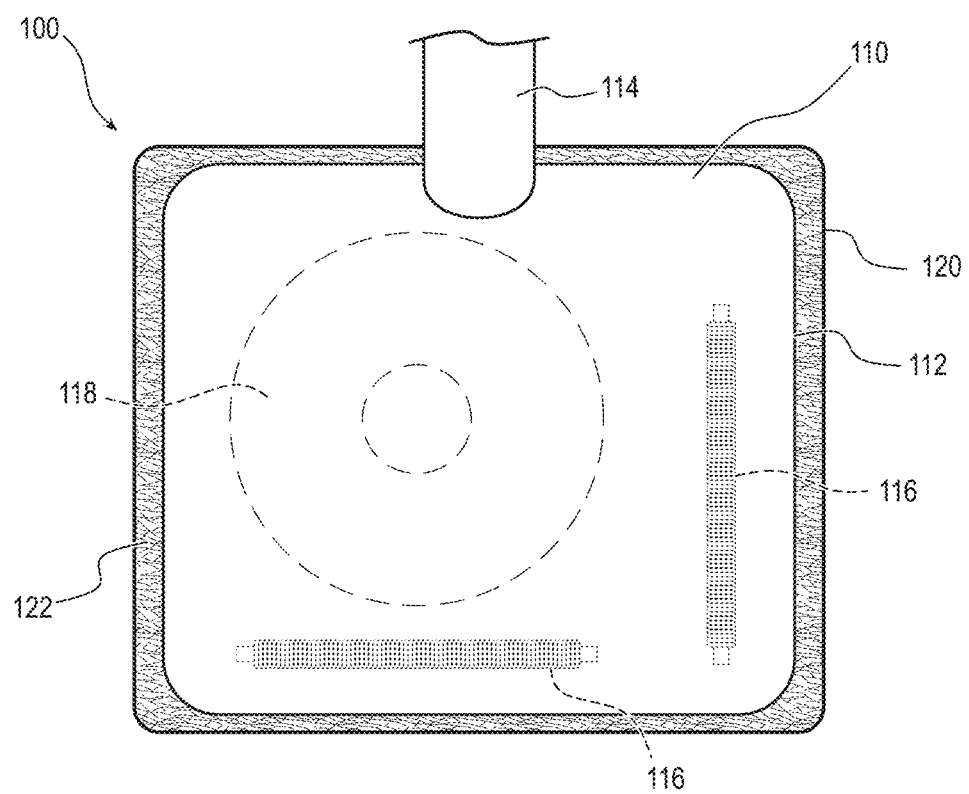
FIG. 2 is a top view of the tracker system of FIG. 1, with tracker coils illustrated in broken lines.

FIGS. 1 and 2 illustrate a tracker system 100 for coupling to tissue 10 for use during a medical procedure to provide a reference point. The tracker system 100 may be used, for example, in Ear, Nose and Throat (ENT) procedures, cranial procedures, spinal procedures, heart procedures, lung procedures, and so forth. FIG. 1 illustrates a side view of the tracker system 100 and FIG. 2 illustrates a top view of the tracker system 100. As also noted above, one or more tracker systems, such as tracker system 100, may be used for patient registration in an image guided navigation system. Registration refers to the computerized process used to match the three-dimensional position of the patient to the pre-operative and intraoperative images that are used for navigation.

The tracker system 100 may include a navigation tracker 110, such as an electromagnetic tracker, coupled to a base pad 120. The navigation tracker 110 may be configured to measure the strength and/or other characteristics of an electromagnetic field induced during a medical procedure, then correlate those measurements to a three-dimensional point in space to provide a reference point. In embodiments wherein the tracker system 100 is fixed to tissue 10 that is closely or tightly coupled to bone, shifting of the tracker system 100 with respect to the bone can be limited or minimized. This may, in turn, minimize shifting of the tracker system 100 with respect to a target area, such as a tumor.

In some embodiments, the target area may be a bone itself. For example, navigation trackers 110 may be attached to several vertebrae. The positions and the orientations of the vertebrae may be tracked via the navigation trackers 110 through a medical procedure that repositions and reorients the vertebrae.

The navigation tracker 110 may comprise a housing 112. The housing 112 may be fabricated from a variety of different materials. For example, the housing 112 may be fabricated of a polymeric material that will not adversely interact with an electromagnetic field. Suitable materials include polyvinyl chloride (PVC), polypropylene (PP), polyethylene (PE), polystyrene (PS), nylon, polyethylene terephthalate (PET), polyimide (PA), polycarbonate (PC), acrylonitrile butadiene (ABS), polyetheretherketone (PEEK), polyurethane (PU) and the like. The housing 112 may be rigid or the housing 112 may be flexible.

The navigation tracker 110 may further comprise a cable 114. The cable 114 may couple the navigation tracker 110 to a computer or other system configured to receive or transmit information from or to the navigation tracker 110 with a point in a reference space. The cable 114 may be electrically coupled to coils (such as trackers 116, 118) within the navigation tracker 110. Current flow through the cable 114 may thus be used to induce a magnetic field around coils (such as trackers 116, 118) and/or to measure current flow induced in the coils (such as trackers 116, 118) when they are subjected to an external magnetic field. The measured current, for example, may then be correlated to a position within the external magnetic field, and thus a point in a reference space.

Additionally, the cable 114 may also be configured to facilitate removal of the tracker system 100 from the tissue 10. The cable 114 may be placed in an asymmetric location, such as near an edge of the navigation tracker 110 to facilitate application of a force to the edge of the navigation tracker 110 and/or the base pad 120. Such a force, applied at an edge, may tend to peel the navigation tracker 110 and/or base pad 120 from the tissue 10, thus facilitating removal.

As noted above, the navigation tracker 110 may comprise trackers 116, 118 disposed within the housing 112. Again, the cable 114 may be electrically coupled to the trackers 116, 118. In some embodiments, the trackers 116, 118 comprise conductive coils, such as metal, that may induce a magnetic field and/or conduct current flow when subject to a magnetic field. In the illustrated embodiment, the navigation tracker 110 includes two different coil designs. Coils 116 are rod coils and coil 118 is a circular coil. However, additional coil designs, shapes, and layouts are likewise within the scope of the present disclosure.

In some embodiments, the trackers 116, 118 may be magnetic field sensors. Example of magnetic field sensors include hall effect sensors, magnetoresistive sensors, tunnel junction sensors, microelectromechanical systems (MEMS), fluxgate sensors, and the like.

In the illustrated embodiment, the housing 112 is coupled to base pad 120 configured to couple the tracker system 100 to tissue. In some embodiments, the base pad 120 is configured to adhere directly to certain tissues. In the illustrated embodiment, the base pad 120 comprises a plurality of nanofibers 122. The nanofibers may be configured to interact directly with the tissue 10 and/or fluids disposed on the surface of the tissue to adhere the base pad 120 to the tissue 10. For example, the nanofibers 122 may be configured to adhere to wet tissue 10 through fluid adsorption, wetting, hydration equilibrium, and/or macromolecular interpenetration.

Absorption is the adhesion of atoms, ions, or molecules from a gas, liquid, or dissolved solid to a surface. Wetting refers to the ability of a liquid to maintain contact with a solid surface, resulting from intermolecular interactions when a liquid and solid surface are brought together. Thus, as the nanofiber 122 of the base pad 120 are brought into contact with moist or wet tissue, the nanofibers 122 tend to stick to the tissue 10 though interaction with moisture on the tissue 10.

Hydration equilibrium may also tend to aid in coupling the base pad 120 to the tissue 10. Hydration equilibrium refers to the tendency of a fluid to move into openings in in a matrix that initially lack the presence of the fluid. In other words, the fluid or liquid in the tissue 10 seeps into the base pad 120 to create an equilibrium between them amount of fluid on the tissue 10 surface and the amount of fluid in the base pad 120.

One or all of absorption, wetting, and hydration equilibrium may for the initial coupling of the base pad 120 to the tissue 10. Macromolecular interpenetration may further couple the base pad 120 to the tissue 10. Macromolecular interpenetration refers to interaction between the plurality of nanofibers 122 and macromolecules on the surface of the tissue 10. These macromolecules may impact surface characteristics to the tissue 10, by making the surface rough or spiny at the nanoscale. Macromolecules in the tissue 10 may penetrate the nanofibers 122 and interact with the nanofibers 122 to adhere or couple the nanofibers 122 to the tissue 10. Examples of macromolecules that may tend to penetrate or otherwise interact with the nanofibers 122 of the base pad 120 include proteins, lipids, macrocycles, and so forth. Further, examples of proteins include glycosylated proteins (mucin, fibrin, etc.), glycoproteins (fibronectin, vitronectin, etc.), and collagen. In some instances, macromolecular interpenetration may be considered as analogous to a hook and loop fastener system in which the macromolecules in the tissue 10 extend into and "hook" around the "loops" formed by the plurality of nanofibers 122.

The nanofibers 122 may be woven or nonwoven. In the illustrated embodiment, the nanofibers 122 are a nonwoven pad with a square shape. However, a number of different pad shapes are within the scope of this disclosure, such as triangular, circular, trapezoidal, polygonal, and the like. The dimensions of the base pad 120 may vary depending of the contemplated use of the tracker system 100 and the type of therapy. In some embodiments, a square base pad 120 may be about 6 mm by 6 mm; however other sizes and shapes are likewise within the scope of this disclosure. For example, one or more dimensions of the base pad may be from about 0.2 mm to about 20 mm, including from about 3 mm to about 15 mm and from about 3 mm to about 10 mm.

The nanofibers 122 may be fabricated from a number of different materials. For example, the nanofibers 122 may be bioabsorbable, bioresorbable, or non-resorbable. In some embodiments, the nanofibers 122 are bioabsorbable. Examples of potential materials include polymers, polylactic acids, Poly-D/L-lactic acid (PDLA), Poly-L/L-lactic acid (PLLA), and so forth. In some embodiments, the nanofibers 122 may have diameters between 10 nanometers and 1 micron. The nanofibers 122 may be formed in a number of different ways. For example, the nanofibers 122 may be formed by drawing, electrospinning, self-assembly, template synthesis, thermal-induced phase separation, and so forth.

The base pad 120 may be coupled to the navigation tracker 110 in a number of different ways. For example, the base pad 120 may be coupled to the navigation tracker 110 by an adhesive 130, such as a gel adhesive. Examples of gel adhesives include but are not limited to synthetic adhesives (such as acrylics, cyanoacrylates, silicone, polyurethanes, etc.), biological adhesives, and so forth. In some embodiments, the navigation tracker 110 may be fabricated out of a material that tends to couple to nanofibers 122 of the base pad 120 without an adhesive. In other words, the nanofibers 122 of the base pad 120 may act as an adhesive themselves to couple the navigation tracker 110 to the base pad 120.

Figure 3:
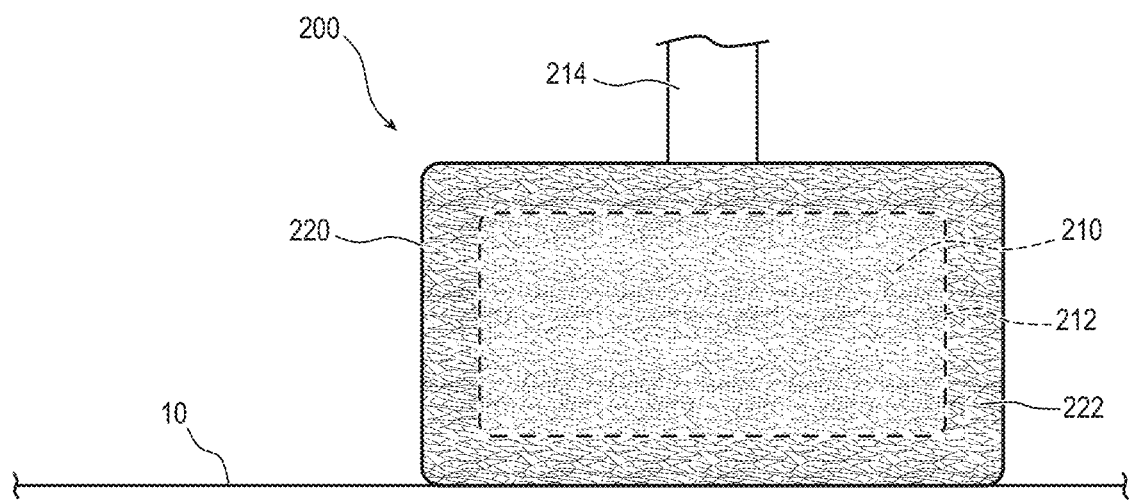
FIG. 3 is a side view of a tracker system disposed within a nanofiber envelope, according to one embodiment of the present disclosure.

FIG. 3 depicts an embodiment of a tracker system 200 that resembles the tracker system 100 described above in certain respects. Accordingly, like features are designated with like reference numerals, with the leading digits incremented to "2." For example, the embodiment depicted in FIG. 3 includes a navigation tracker 210 that may, in some respects, resemble the navigation tracker 110 of FIGS. 1 and 2. Relevant disclosure set forth above regarding similarly identified features thus may not be repeated hereafter. Moreover, specific features of tracker system 100 and related components shown in FIGS. 1 and 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the tracker system 200 and related components depicted in FIG. 3. Any suitable combination of the features, and variations of the same, described with respect to the tracker system 100 and related components illustrated in FIGS. 1 and 2 can be employed with the tracker system 200 and related components of FIG. 3, and vice versa. This pattern of disclosure applies equally to further embodiments depicted in subsequent figures and described hereafter, wherein the leading digits may be further incremented.

FIG. 3 illustrates a tracker system 200 that includes an navigation tracker 210 disposed fully within a base pad 220. In other words, the base pad 220 encompasses or envelopes the navigation tracker 210. In other embodiments, the navigation tracker 210 may be an electromagnetic tracker, an infrared tracker, a radio tracker, or an ultrasound tracker.

In the illustrated embodiment, the navigation tracker 210 is a rectangular prism. Embodiments wherein the navigation tracker 210 is a cube or other shapes are likewise within the scope of this disclosure. For example, the navigation tracker 210 may be a 3 mm by 3 mm by 3 mm cube, a 6 mm by 6 mm by 6 mm cube, or any other shape where one or more sides are from about 0.2 mm to about 20 mm. Embodiments wherein the base pad 220 is disposed all around, or substantially all around, the navigation tracker 210 may facilitate coupling of the navigation tracker 210 to tissue, as all sides of the navigation tracker 210 may tend to adhere to tissue 10. In some embodiments, all portions of the exterior of the navigation tracker 210 other than the cable 214 may be covered with nanofibers. In some embodiments, the navigation tracker 210 may include three orthogonal coils (not shown) disposed within the navigation tracker 210. However, the navigation tracker 210 may include more or fewer than three coils.

In some embodiments, the navigation tracker 210 may have a cuboid shape. For example, the dimensions of the cuboid may be a 5 mm by 5 mm base with a 1 mm height. Again, various dimensions are within the scope of this disclosure, include base measurements from about 3 mm to about 20 mm and height measurements of more or less than 1 mm for cuboid forms.

The dimensions noted above are illustrative in nature and not limiting. For example, some tracker systems may be larger or smaller. For example, in some embodiments, the navigation tracker 210 may be designed to house a single coil. In such embodiments, the navigation tracker 210 may have an outer diameter such as 0.2 mm and a length of 2 mm to house a single coil. Again, other sizes and dimensions are also contemplated.

Figure 4:
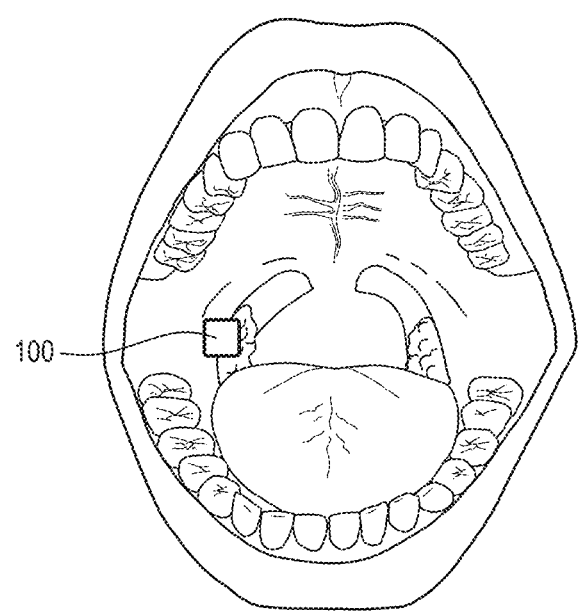
FIG. 4 illustrates a tracker system adhered to oral mucosa of a patient according to one embodiment of the present disclosure.
Figure 5:
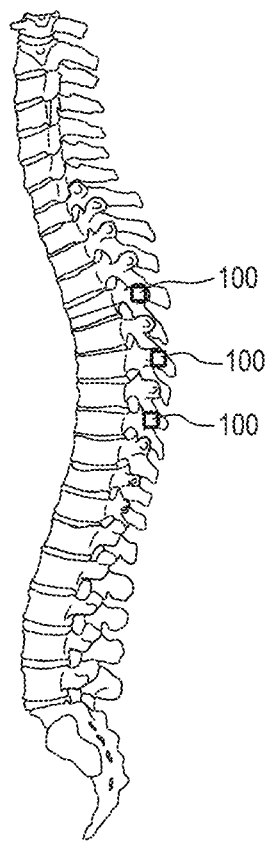
FIG. 5 illustrates a tracker system adhered to bone periosteum of the spine of a patient according to one embodiment of the present disclosure.

As noted above, in some procedures, coupling of a tracker system (such as 100 and 200) wet relatively immobile tissue, such as oral mucosa (gums), bone periosteum, and so forth may facilitate a variety of procedures. FIG. 4 illustrates the tracker system 100 (of FIG. 1) coupled to oral mucosa. FIG. 5 illustrates the tracker system 100 coupled to bone periosteum of cortical bone of the spine. In other embodiments, the tracker system 100 may be adhered other tissue, including softer tissue that may have more flex or stretch to it, such as the brain, lungs, heart, and so forth. While the illustrated embodiments in FIGS. 4 and 5 illustrate a single tracker system 100, multiple tracker systems 100 may be placed along portions of a patient's body for a single medical procedure. These may be used to track the patient, the relative location and orientation of spine segments, brain shift, lung respiration, heart pulsation, and the like.

In some embodiments, the tracker system 100 may include radiopaque patterns disposed on or within the base pad 120. For example, a portion of the nanofibers 122 of the base pad 120 may be radiopaque, thus creating an X-ray, a CT, or an MRI imagable pattern that a medical practitioner may identify during the medical procedure. In some embodiments, an automated system is configured to locate and identify the pattern. In some embodiments, a portion of the nanofibers 122 of the base pad 120 are arranged in a radiopaque that the medical practitioner may identify during the medical procedure. In some embodiments, an automated system is configured to locate and identify the pattern. For example, the pattern may be a square, a star, a series of parallel lines, triangle, circle, and the like. The automated system may register the pattern with an MRI image of the procedure.

When the base pad 120 becomes wetted, the base pad 120 shows up in MRI images due to the water content of the base pad 120. In some embodiments, a portion of the nanofibers 122 may be fabricated from a radiopaque material or polymer. Such radiopaque nanofibers may be placed in a pattern or shape to facilitate recognition via an X-ray, a CT, or an MRI image or to distinguish between multiple markers in one image. In some embodiments, a radiopaque agent may be added to the material or polymer to fabricate the nanofibers 122, thus making the nanofibers 122 radiopaque.

Multiple tracker systems 100 may be used during a single medical procedure. The multiple tracker systems 100 may each have a distinct pattern so that the medical practitioner knows what pattern is associated with each tracker system 100. In some embodiments, an automated system is configured to locate and identify the pattern. As the different tracker systems 100 may be adhered to tissue during the procedure, the medical practitioner knows which tracker system is associated in a three-dimensional space to help the medical practitioner navigate during the procedure.

Figure 6:
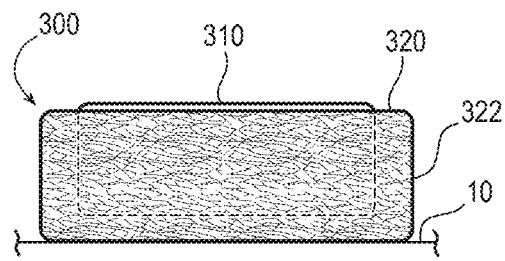
FIG. 6 is a side view of a tracker system according to one embodiment of the present disclosure.
Figure 7:
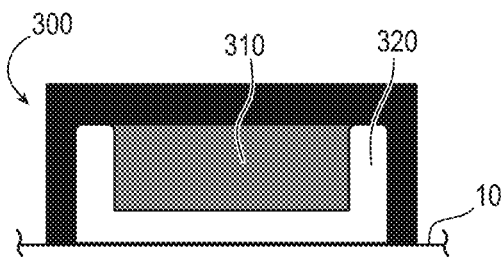
FIG. 7 is a schematic representation of an image (such as an X-ray, a CT, or an MRI image) of the tracker system of FIG. 6.

FIGS. 6-9 depict two embodiments of tracker systems that produce an X-ray, a CT, or an MRI imagable pattern. FIG. 6 illustrates a tracker system 300 that includes a navigation tracker 310 that is partially disposed within a base pad 320. In some embodiments, the navigation tracker 310 may be an electromagnetic tracker, an infrared tracker, a radio tracker, or an ultrasound tracker. The base pad 320 comprises a plurality of nanofibers 322 that are radiopaque. FIG. 7 is a schematic representation of the tracker system 300 as an X-ray, a CT, or an MRI image. For example, the radiopaque nanofibers 322 of the base pad 320 may create a substantially U-shape cross-sectional pattern or image that the medical practitioner may identify during the medical procedure. Other patterns or images may be seen when viewed from different two dimensional views or three dimensional reconstructions.

Figure 8:
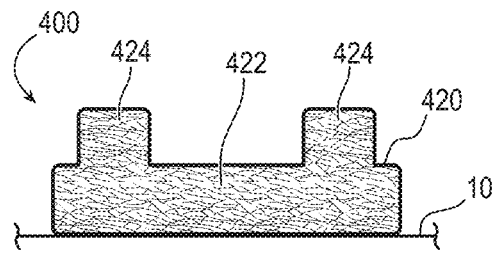
FIG. 8 is a side view of a tracker system according to one embodiment of the present disclosure.
Figure 9:
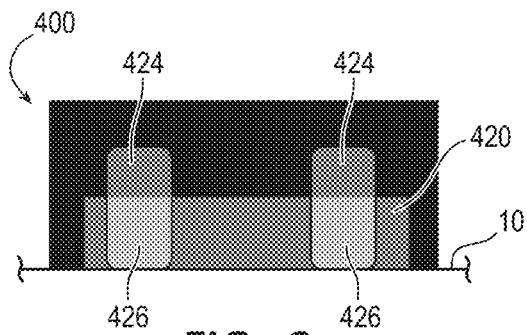
FIG. 9 is a schematic representation of an image (such as an X-ray, a CT, or an MRI image) of the tracker system of FIG. 8.

In some embodiments, the trackers (e.g., metal coils) are disposed directly in the base pad and not in a separate tracker housing. FIG. 8 illustrates a tracker system 400 with a base pad 420 that comprises a plurality of nanofibers 422. The illustrated embodiment of the tracker system 400 does not include a tracker housing, and the tracker (e.g., metal coil) may be disposed directly within the base pad 420. However, the tracker system 400 may include a tracker disposed between the side walls 424. The base pad 420 may further include a pair of side walls 424 that are disposed a predetermined distance from the edge of the base pad 420. The nanofibers 422 that overlap between the side walls 424 and the base pad 420 may be radiopaque. FIG. 9 is a schematic representation of an image of the tracker system 400 as an X-ray, a CT, or an MRI image. The radiopaque nanofibers 422 of the base pad 420 create rectangular shapes 426 or images that the medical practitioner may identify during the medical procedure. In some embodiments, an automated system is configured to locate and identify the pattern.

Figure 10:
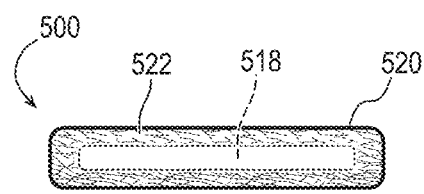
FIG. 10 is a side view of a tracker system according to one embodiment of the present disclosure.
Figure 11:
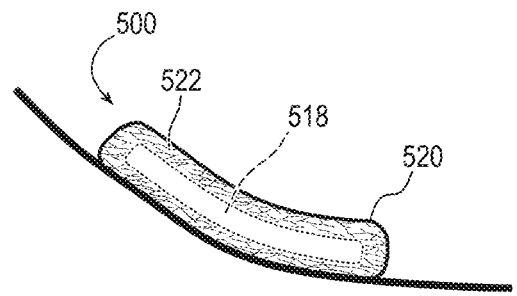
FIG. 11 is a side view of the tracker system of FIG. 10 attached to a curved tissue surface, the tracker system being conformable to the tissue surface.

As shown in FIGS. 10-13, in some embodiments, a tracker system 500 may be conformable. This is facilitates coupling when the tracker system 500 is adhered to tissue 10 that is not flat or in situations in which a tracker system 600 is adhered between two wet tissues 10, 20. FIG. 10 illustrates a side view of a tracker system 500. The tracker system 500 may include a tracker 518 (e.g., metal coil) that is disposed within a base pad 520 of nanofibers 522 without a separate tracker housing. The base pad 520 may have a cuboid shape with the tracker 518 disposed within. However, the base pad 520 may have a number of different shapes within the scope of this disclosure. FIG. 11 illustrates the tracker system 500 adhered to a non-flat wet tissue 10 in which the shape of the base pad 520 and the shape of tracker 518 conform to the shape of the non-flat wet tissue 10. While not illustrated in FIGS. 10 and 11, the tracker system 500 may further include a cable to power to the tracker 518 or communicate signals as discussed above.

Figure 12:
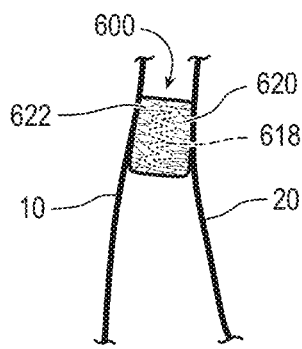
FIG. 12 is a side view of a tracker system that is attached between two tissues surfaces according to one embodiment of the present disclosure.
Figure 13:
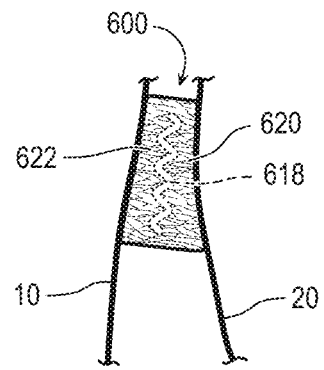
FIG. 13 is a side view of the tracker system of FIG. 12 attached between two tissue surfaces, the tracker system being conformable between the two tissue surfaces.

FIG. 12 illustrates a tracker system 600 that includes a tracker 618 (e.g., metal coil) that is disposed within a base pad 620 without a separate tracker housing. The base pad 620 may have a cuboid shape with the tracker 618 disposed within. However, the base pad 620 may have a number of different shapes within the scope of this disclosure. The tracker system 600 is shown adhered between two wet tissues 10, 20. FIG. 13 illustrates that tracker system 600 conforming to the shape between the two wet tissues 10, 20. The tracker system 600 may expand due to wicking and/or application of saline, etc. In other words, the base pad 620 expands to conform to the two tissues 10, 20 and the coil is configured to expand and lengthen relative to the expansion of the base pad 620.

Figure 14:
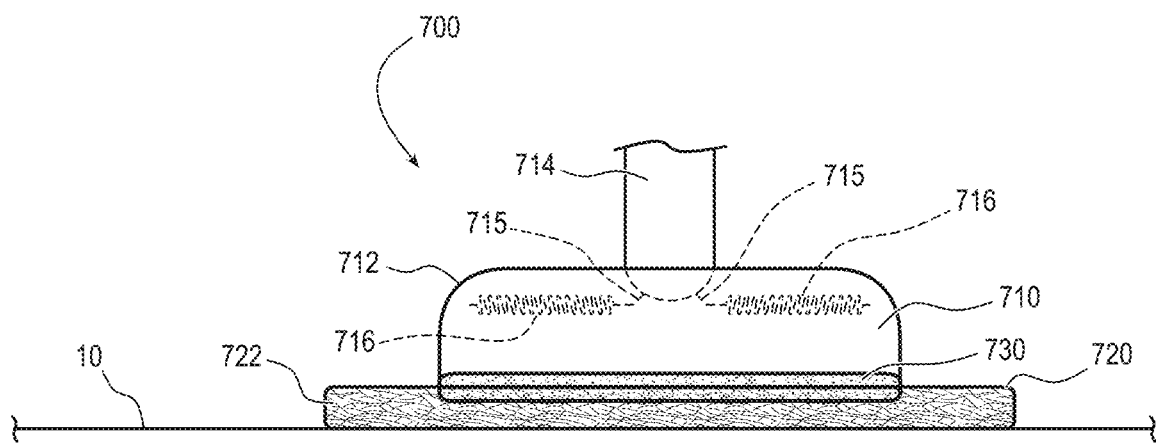
FIG. 14 is a side view of a tracker system adhered to a tissue of a patient according to one embodiment of the present disclosure.
Figure 15:
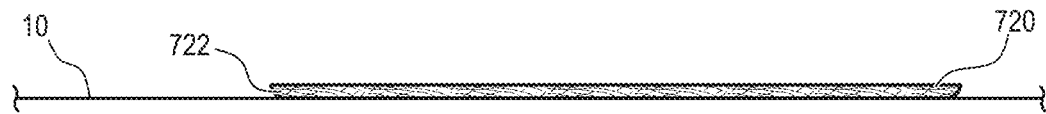
FIG. 15 is a side view of a portion of a base pad of the tracker system of FIG. 14, after the tracker system is removed from the tissue of the patient.

FIGS. 14 and 15 illustrate one process of removing a tracker system 700 that is adhered to tissue 10. FIG. 14 illustrates the tracker system 700 that includes a navigation tracker 710 that is coupled to a base pad 720 via an adhesive 730. In some embodiments, the navigation tracker 710 may be an electromagnetic tracker, an infrared tracker, a radio tracker, or an ultrasound tracker. The base pad 720 comprises a plurality of nonwoven nanofibers 722 that adhere to the tissue 10. As discussed above, the tissue 10 may be immobile or mobile tissue. The nanofibers 722 of the base pad 720 are configured to adhere to wet tissue 10 in a number of different ways, such as adsorption, wetting, hydration equilibrium, and macromolecular interpenetration. In other words, the plurality of nanofibers 722 may interact with the tissue 10 to couple the base pad 720 to the tissue 10.

The navigation tracker 710 may comprise a housing 712 and a cable 714 that extends into the housing 712 of the navigation tracker 710. Disposed within the housing 712 may be a plurality of trackers 716. In the illustrated embodiment, the trackers 716 may be conductive coils, such as metal. The trackers 716 are in electrical communication with the cable 714. A first end of the cable 714 is coupled to a power source, computer, signal reader, or so forth and a second end of the cable 714 comprises leads 715. The leads 715 are in communication with leads of the trackers 716 to provide power to the trackers 716 or conduct a signal or current away from the trackers 716.

As noted in other embodiments, the cable 714 may also facilitate removal of the tracker system 700 from the tissue 10. The cable 714 may be placed in an asymmetric location to help remove the navigation tracker 710 from the base pad 720. The asymmetric location of the cable 714 may enables the medical practitioner to pull the cable 714 in a way that tends to peel the base pad 720 from the tissue 10. In some embodiments, a portion of the base pad 720 may remain on the tissue 10, as illustrated in FIG. 15. In some embodiments, the cable 714 may be placed in a symmetric location.

Thus, after some therapies, a portion of the base pad 720 may remain adhered to the tissue 10 while a portion of the base pad 720 remains coupled to the navigation tracker 710. As discussed previously, if the nanofibers 722 of the base pad 720 are fabricated from bioabsorbable nanofibers, then the portion of the base pad 720 that remains adhered to the tissue 10 will be reabsorbed by the body of the patient.

Figure 16:
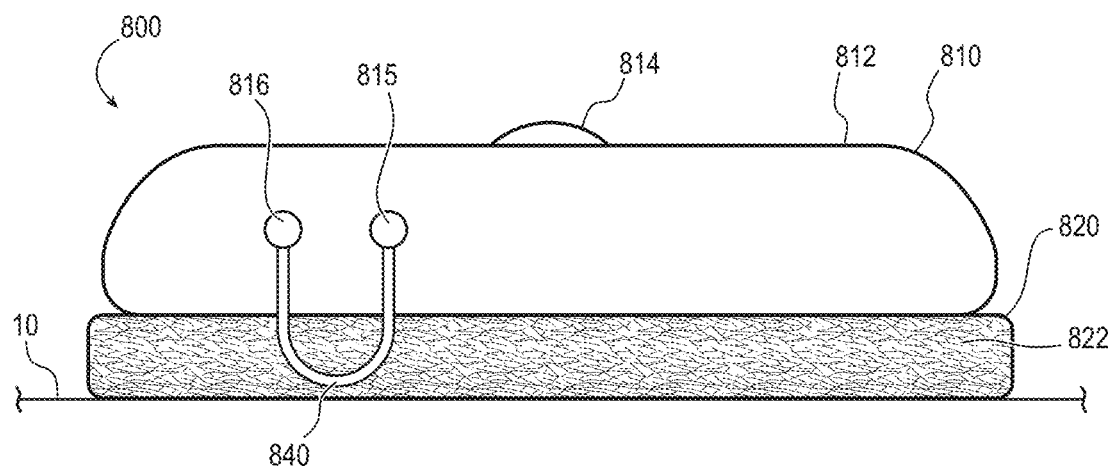
FIG. 16 is an end view of a tracker system adhered to a tissue of a patient according to another embodiment of the present disclosure.
Figure 17:
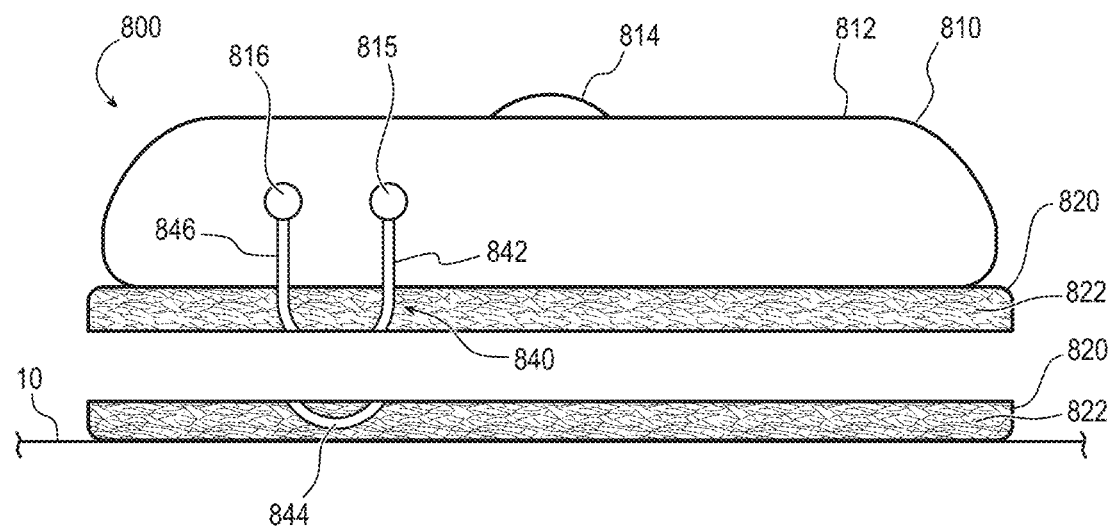
FIG. 17 is an end of view of the tracker system of FIG. 16, after the tracker system is removed from the tissue of the patient, showing a portion of a base pad of the tracker system adhered to the tissue.

FIGS. 16 and 17 illustrate the process of removing another tracker system 800 that is adhered to tissue 10. FIG. 16 illustrates the tracker system 800 that includes an navigation tracker 810 that is coupled to a base pad 820. In some embodiments, the navigation tracker 810 may be an electromagnetic tracker, an infrared tracker, a radio tracker, or an ultrasound tracker. The tracker system 800 does not illustrate that the base pad 820 is coupled via an adhesive. However, the use of an adhesive to couple the navigation tracker 810 to the base pad 820 is within the scope of the present disclosure as well as embodiments with no such separate adhesive. The base pad 820 may comprise a plurality of nonwoven nanofibers 822 that tend to adhere to tissue 10.

The navigation tracker 810 may comprise a housing 812 and a cable 814 that extends into the housing 812 of the navigation tracker 810. Disposed within the housing 812 may be a plurality of trackers 816. In the illustrated embodiment, the navigation tracker 810 comprises a single tracker 816, which may be a conductive coil, such as metal. FIG. 16 is an end view of the tracker 816, not a side view, like FIG. 14. The tracker 816 is in electrical communication with the cable 814 via a lead 815 of the cable 814. A first end of the cable 814 is coupled to a power source and a second end of the cable 814 comprises the lead 815 that provides power to the tracker 816. When power or current is provided to the tracker 816 (e.g., conductive coils), the tracker 816 produces an electromagnetic field. Similarly, measurement of current across the coil may be used to detect position with an external electric field.

The tracker system 800 may comprise a conductive pathway 840 that connects a lead of the tracker 816 with the lead 815 of the cable 814. The conductive pathway 840 may comprise a path that traverses a portion of the base pad 820.

Again, in the illustrated embodiment, the conductive pathway 840 starts at the lead 815 of the cable 814 and then enters the base pad 820. The conductive pathway 840 extends relatively deep into the base pad 820 before returning back into the navigation tracker 810. After entering the navigation tracker 810, the conductive pathway 840 connects to the lead of the tracker 816. The illustrated embodiment only illustrates the single tracker 816; however, the navigation tracker 810 may comprise a plurality of trackers 816 and the conductive pathway 40 connects the leads of each tracker 816 with the lead 815 of the cable 814. The conductive pathway 840 may be fabricated from a number of different materials. For example, the conductive pathway may be a conductive adhesive or bioresorbable metals such as magnesium.

The cable 814 may also serve as a removal device to remove the tracker system 800 from the tissue 10. The cable 814 may be located in an asymmetric location to help remove the navigation tracker 810 from the base pad 820. The asymmetric location of the cable 814 enables the medical practitioner to pull the cable 814 in a proximal direction to remove the navigation tracker 810 from the base pad 820 as illustrated in FIG. 17.

During or after this removal, a portion of the base pad 820 may remain adhered to the tissue 10 while a portion of the base pad 820 may remain coupled to the navigation tracker 810. As discussed previously, if the nanofibers 822 of the base pad 820 are fabricated from bioabsorbable nanofibers, then the portion of the base pad 820 that remains adhered to the wet tissue 10 will be reabsorbed even though it was left adhered to the tissue 10.

In the example of FIGS. 16-17, when the navigation tracker 810 is removed from the base pad 820, a portion of the conductive pathway 840 may remain in the portion of the base pad 820 that is adhered to the tissue 10. As illustrated in FIG. 17, a first portion 842 of the conductive pathway 840 is disposed within the navigation tracker 810 and the portion of the base pad 820 that was removed from the tissue 10. A second portion 844 of the conductive pathway 840 is disposed within the portion of the base pad 820 that remains adhered to the tissue 10. A third portion 846 of the conductive pathway 840 is disposed within the navigation tracker 810 and the portion of the base pad 820 that was removed from the tissue 10.

The above-described arrangement of the conductive pathway 840 may provide several benefits. For example, the trackers 816 can receive power or measure current from the cable 814 only if the circuit is complete between the lead 815 of the cable 814 to the trackers 816. Therefore, the medical practitioner may track if the circuit is broken during the procedure. For example, the circuit may be broken through the misalignment between the navigation tracker 810 and the base pad 820 or if the navigation tracker 810 and the base pad 820 have been prematurely separated.

In addition, when the medical procedure is ending, the medical practitioner may remove the navigation tracker 810 from the base pad 820. The medical practitioner will be able to confirm when the circuit is broken because the circuit will be broken when the navigation tracker 810 is removed from the base pad 820.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A tracker system for coupling to wet, immobile tissues comprising:
   a nanofiber base pad formed from a plurality of nanofibers; and
   a navigation tracker coupled to the base pad;
   wherein the nanofiber base pad has a first tissue engaging surface configured to directly engage the tissue and an opposed navigation tracker surface configured to directly engage the navigation tracker;
   wherein a portion of the nanofiber base pad and a portion of the navigation tracker are electrically coupled by a breakable conductive pathway formed of conductive material extending between the nanofiber base pad and the navigation tracker;
   wherein the conductive material extending between the nanofiber base pad and the navigation tracker is broken upon separating the navigation tracker from at least a portion of the nanofiber base pad.

2. The tracker system of claim 1, wherein the navigation tracker is coupled to the nanofiber base pad by a gel adhesive.

3. The tracker system of claim 1, wherein the nanofiber base pad comprises nonwoven nanofibers.

4. The tracker system of claim 3, wherein the nanofibers have a diameter between 10 nanometers and 1,000 nanometers.

5. The tracker system of claim 3, wherein the nanofibers are bioabsorbable.

6. The tracker system of claim 3, wherein a material of the nanofibers are one of polylactic acids, poly-OIL-lactic acid, and Poly-LIL-lactic acid.

7. The tracker system of claim 3, wherein the nanofibers are electrospun.

8. The tracker system of claim 3, wherein a portion of the nanofibers are radiopaque.

9. The tracker system of claim 1, wherein a portion of the plurality of nanofibers of the base nanofiber pad are arranged in a radiopaque pattern.

10. The tracker system of claim 9, wherein the radiopaque patterns register with an image of the procedure.

11. The tracker system of claim 1, wherein the navigation tracker is at least one of a radio tracker, an infrared tracker, and an ultrasound tracker.

12. The tracker system of claim 1, wherein the conductive pathway is a conductive adhesive pathway that extends from the navigation tracker into the nanofiber base pad.

13. The tracker system of claim 1, wherein the nanofiber base pad is configured to conform to the tissue.

14. The tracker system of claim 1, wherein the nanofiber base pad is electrically conductive.

15. The tracker system of claim 1, wherein the conductive pathway extends from the navigation tracker into the nanofiber base pad.

16. The tracker system of claim 15, wherein the conductive pathway further extends from the nanofiber base pad back into the navigation tracker.

17. The tracker system of claim 15, wherein the navigation tracker comprises at least one conductive coil disposed within the navigation tracker, wherein the conductive pathway extends from a cable to the nanofiber base pad and then to the at least one conductive coil disposed within the navigation tracker.

18. The tracker system of claim 17, wherein a circuit between the cable and the at least one conductive coil is broken when the conductive pathway is broken as the navigation tracker is decoupled from the base pad.

19. The tracker system of claim 1, wherein the tracker system further comprises a transmitter.

20. The tracker system of claim 1, wherein the navigation tracker is an electromagnetic tracker, the system further comprising a cable coupled to the electromagnetic tracker, wherein the cable provides power to activate the electromagnetic tracker.

21. The tracker system of claim 1, wherein the nanofiber base pad is configured to couple to the wet tissue of a subject via at least one of absorption, hydration equilibrium, and macromolecular interpenetration.

* * * * *